United States Patent [19]

Goor et al.

[11] Patent Number: 4,821,735

[45] Date of Patent: Apr. 18, 1989

[54] METHOD AND APPARATUS FOR DETECTING MYOCARDIAL ISCHEMIA

[76] Inventors: Daniel Goor, Rehov David Hemelech 47, Tel Aviv; Raphael Mohr, Rehov Hameshorer 10, Kiryat Krinitzi, Ramat Gan, both of Israel

[21] Appl. No.: 153,498

[22] Filed: Feb. 11, 1988

Related U.S. Application Data

[63] Continuation of Ser. No. 856,489, Apr. 25, 1986, abandoned.

[30] Foreign Application Priority Data

Jan. 22, 1986 [IL] Israel .......................................... 77677

[51] Int. Cl.⁴ ................................................ A61B 5/02
[52] U.S. Cl. .................................... 128/713; 128/672; 128/675
[58] Field of Search ................ 128/713, 668, 672–675, 128/677

[56] References Cited

U.S. PATENT DOCUMENTS

4,203,451  5/1980  Panico ................................. 128/672

*Primary Examiner*—Lee S. Cohen
*Attorney, Agent, or Firm*—Hale and Dorr

[57] ABSTRACT

An apparatus and method for detecting myocardial ischemia in a subject monitors the systemic vascular resistance of the subject and detects the presence of myocardial ischemia when the systemic vascular resistance increases by at least sixty percent over a base line value. Particular apparatus describe providing a measurement corresponding to the systemic vascular resistance of the cardiovascular system. A particular invasive pressure measuring apparatus uses a flexible catheter tube insertable into the artery of the subject and a micro-manometer embedded into the outer face of the wall of the catheter tube. The outer face of the embedded micro-manometer is directly exposed to the blood in an artery and the inner face of the embedded micro-manometer is covered by the inner face of the catheter tube wall.

6 Claims, 1 Drawing Sheet

METHOD AND APPARATUS FOR DETECTING MYOCARDIAL ISCHEMIA

This is a continuation of co-pending application Ser. No. 856,489 filed on Apr. 25, 1986, now abandoned.

BACKGROUND OF THE INVENTION

The present invention relates to a method and apparatus for detecting myocardial ischemia.

Myocardial ischemia can be defined as a decreased supply of blood to the heart, and more precisely as an imbalance between the myocardial oxygen supply and demand. In most clinical situations, the reason for this imbalance is inadequate perfusion (blood injection) of the myocard (muscle tissue of the heart) due to obstructions or stenosis (a narrowing) of the coronary arteries (the arteries that supply blood to the heart). The ischemia can last only a few seconds or it can persist for minutes or even hours, causing transient or permanent damage to the heart muscle (myocardial infarction). Myocardial ischemia is usually accompanied by chest pain (angina). In some cases, however, it is not accompanied by pain, or the subject is not aware of the pain, for example, when the subject is unconscious, and therefore detection of the ischemia must be made by objective methods rather than by relying on complaints of the subject.

The most commonly used objective criteria for ischemia detection and monitoring are the electrocardiographic (ECG) changes at rest or during effort testing. Ischemia can be demonstrated by the elevation or depression of the S-T segment, by inversion or other changes in T-waves, or by changes in the shape or width of the QRS complex. However, sometimes electrocardiographic changes are not detected because the appropriate electrocardiograph lead (of the 12 commonly used leads) is not being monitored. At other times, the electrocardiograph is too sensitive and reflects changes that have no real significance.

For these reasons, methods other than use of the ECG, are employed to detect myocardial ischemia. These other methods include:

a. Hemodynamic Changes Associated with Ischemia—subject's blood pressure. Blood pressure can therefore also be used for continuously monitoring for myocardial ischemia. This method is commonly used in operating rooms; and it is good cardiac anesthesia practice to prevent increases and decreases of blood pressure as much as possible. However, changes in blood pressure can result from pain or from other reasons; and therefore, changes in blood pressure alone are unreliable as the primary indicator of ischemia.

Another commonly used hemodynamic parameter is the pressure in the left atrium. This parameter can be monitored indirectly, for example, by using a Swann-Ganz catheter which measures the pulmonary-capillary wedge pressure that is usually equal to the left atrial pressure. Left atrial pressure can also be measured directly after open heart procedures through a catheter introduced into the left atrium. In catheterization laboratories, the left ventricular end diastolic pressure (LVEDP) can be measured through a catheter introduced through the aorta. Changes in left atrial pressure usually reflect changes in LVEDP, and ischemia is usually associated with increased LVEDP. Because of the highly invasive nature of the pressure measurements of the left atrium, pulmonary-capillary wedge, or of the left ventricle, these methods are used only in special situations. It is also important to note that ischemia is not always associated with increased LVEDP.

b. Two-Dimensional Echocardiography—Important changes in ventricular wall motions or in ventricular dimensions are associated with ischemia. Two-dimensional echocardiography, using external transducers, can detect increased left ventricular end diastolic and end systolic volume. A trans-esophageal echocardiographic transducer allows continuous detection and monitoring of changes in ventricular wall motion, and therefore also enables monitoring of ischemia.

c. Radionuclide Ventriculography—Injection of radioactive marker (Tc-99n phyrophosphate stanus) that adheres to the myocardial muscle provides a method for monitoring changes in ventricular wall motion, and therefore also enables detection of ischemia. This method for the non-invasive detection of ischemia is used during rest and effort tests.

d. Thalium 201H perfusion scans provide a further method for the selective and non-invasive monitoring of the blood supply to the heart. Although radionuclide ventriculography and Thalium perfusion scans can detect ischemia, they both involve large and expensive instruments, and therefore these methods are not commonly used for monitoring of ischemia.

An object of the present invention is therefore to provide a new method and apparatus for detecting myocardial ischemia.

SUMMARY OF THE INVENTION

According to one aspect of the present invention, there is provided a method for detecting myocardial ischemia in a subject comprising monitoring the systemic vascular resistance of the subject, and detecting when the systemic vascular resistance increases by at least 60% to thereby indicate the presence of myocardial ischemia.

The systemic vascular resistance (SVR) of a subject is the total peripheral resistance (TPR) of the subject's cardiovascular system. Measurements of the subject's systemic vascular resistance, together with other measurements, are commonly made in order to assess the status of the subject's cardiovascular system, particularly in monitoring post-operation recovery of patients. Some of the other measurements presently made in assessing the status of the subject's cardiovascular system include the mean arterial pressure (MAP), central venous pressure (CVP), and cardiac output (CO). All these measurements have the following relationship:

$$MAP - CVP = CO \times SVR$$

This relationship will be recognized as the cardiovascular equivalent of Ohm's law of electricity, E (voltage) = I (current) × R (resistance).

A number of techniques are known for measuring systemic vascular resistance. Particularly good results have been obtained when the method described in our U.S. Pat. No. 4,429,701, the disclosure of which is incorporated herein, in its entirety, by reference, is used. This method is broadly characterized by the following steps:

A. detecting the arterial pressure of the subject and generating in response thereto a blood pressure signal having a waveform in accordance with the detected arterial pressure;

B. differentiating the blood pressure signal to produce a dP/dt signal having a waveform varying in accordance with the rate at which the blood pressure signal varies;

C. detecting the peak of the dP/dt signal to determine the peak dP/dt;

D. determining a value which is substantially equal to the arterial pressure at the time of said peak dP/dt; and E. dividing said latter value by the peak dP/dt signal, which thereby produces a measurement corresponding to the systemic vascular resistance of the cardiovascular system.

While we have found that an increase of at least 60% in the systemic vascular resistance is strongly indicative of myocardial ischemia, we have also found that most cases of myocardial ischemia are accompanied by an increase of at least 100% in the systemic vascular resistance, usually between 100–200%, but sometimes up to 400% and even more.

We have found that myocardial ischemia can be detected accurately when using only one channel, rather than the two channels described in the above-cited patent specification. We have also found that the radial artery is too sensitive, and that best results are obtained when using a centrally located artery, preferably the femoral artery.

Our invention also provides apparatus for detecting myocardial ischemia in accordance with the above method.

According to a further aspect of the invention, there is provided apparatus particularly useful in detecting myocardial ischemia in accordance with an invasive technique for practicing the above method. The apparatus employs a flexible catheter tube, which can be inserted into the artery of the subject, and a micromanometer (pressure transducer) embedded in the outer face of the catheter tube wall. Best results have been obtained when the outer face of the embedded micro-manometer is directly exposed to the blood in the artery, with the inner face of the embedded micro-manometer covered by the inner face of the catheter tube wall, and when the micro-manometer is embedded in the distal tip of the catheter tube. There may also be used a balloon dilatation catheter receivable through the catheter tube during percutaneous coronary angioplasty (PTCA).

While such an invasive technique has been found to produce best results, it is conceivable that a non-invasive technique, such as by using pressure cuffs, may also be used for monitoring the systemic vascular resistance in order to detect myocardial ischemia in accordance with the above method and apparatus.

BRIEF DESCRIPTION OF THE DRAWINGS

Other objects, features and advantages of the invention will be apparent from the following description, with reference to the accompanying drawings, in which.

DESCRIPTION OF A PREFERRED EMBODIMENT

Figure 1:
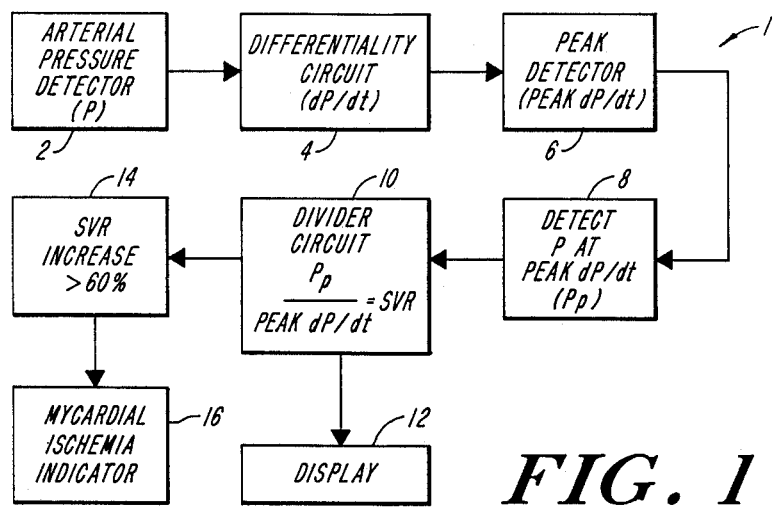
FIG. 1 is a block diagram illustrating a preferred apparatus constructed in accordance with the invention for detecting myocardial ischemia.

Referring to FIG. 1, a system 1 monitors the systemic vascular resistance of a subject in accordance with the method and apparatus described in U.S. Pat. No. 4,429,701 which is incorporated herein by reference. Briefly, the system includes an arterial pressure detector 2 detecting the blood-pressure (P) of the subject and generating in response thereto a blood-pressure signal having a waveform in accordance with the detected arterial pressure; a differentiating circuit 4 differentiating the blood-pressure signal (P) to produce a signal (dP/dt) having a waveform varying in accordance with the rate at which the blood-pressure signal (P) varies; a peak detector circuit 6 detecting the peak of the dP/dt signal and producing a corresponding signal (peak dP/dt); a circuit 8 for determining a value ($P_P$) which is substantially equal to the arterial pressure at the time of the peak dP/dt signal; and a divider circuit 10 for dividing the latter value ($P_P$) by the (peak dP/dt) signal. The output of circuit 10 is a value which corresponds to the systemic vascular resistance (SVR) of the subject's cardiovascular system. The systemic vascular resistance so determined is displayed in a display unit 12.

Circuit 8, which determines a value substantially equal to the arterial pressure at the time of the peak dP/dt signal, can detect the actual arterial pressure at the time of the peak dP/dt, or can detect merely the diastolic pressure, since the diastolic pressure is substantially equal to the arterial pressure at the time of the peak dP/dt. Further particulars with respect to the apparatus and method illustrated in FIG. 1 for measuring the systemic vascular resistance are described in the above-identified U.S. Pat. No. 4,429,701.

As noted above, we have discovered that when the systemic vascular resistance increases substantially, by at least 60%, it is strongly indicative of the presence of a myocardial ischemic episode. Accordingly, the system illustrated in FIG. 1 includes a circuit 14 which determines when the systemic vascular resistance value output from circuit 10 has increased by at least 60%, and when this has been found to be the case, an indicator 16, such as an alarm, is actuated to indicate the probability of myocardial ischemia.

As mentioned earlier, while a 60% increase in the systemic vascular resistance is strongly indicative of myocardial ischemia, in most cases where myocardial ischemia has been found to exist, the systemic vascular resistance increased over 100%, usually from 100–200%, but sometimes even as much as 400% or more. The higher the increase, the greater the probability that a myocardial ischemic episode exists.

Figure 2:
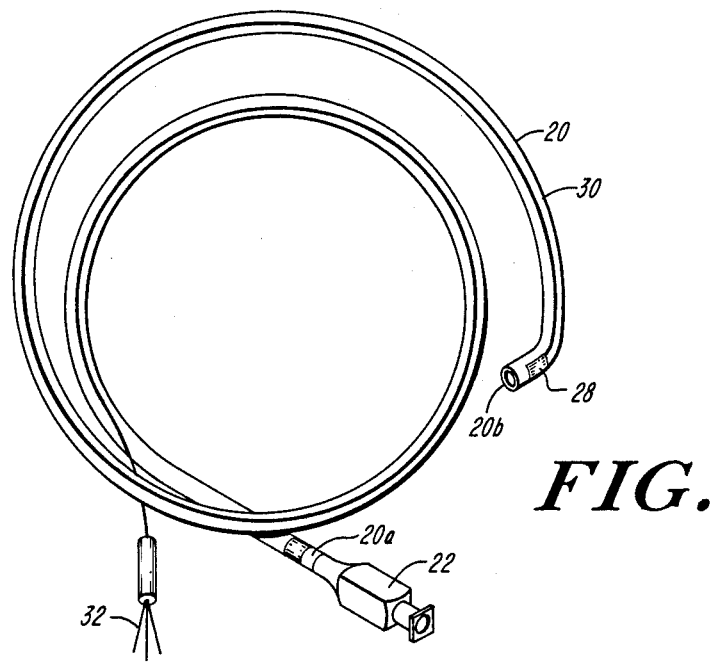
FIG. 2 illustrates a flexible catheter tube particularly useful with the apparatus of FIG. 1.
Figure 3:
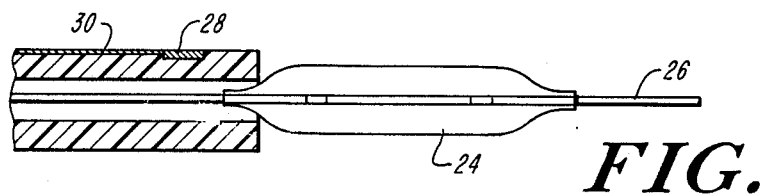
FIG. 3 is an enlarged fragmentary view illustrating the use of a coronary balloon dilatation catheter with the catheter tube of FIG. 2.

FIGS. 2 and 3 illustrate a device particularly useful for the arterial pressure detector 2 of FIG. 1 for measuring the arterial blood pressure (P).

The illustrated device includes a flexible catheter tube 20 insertable into the artery of the subject. A fitting 22 is carried at a proximal end 20a of the catheter tube 20 for the insertion of a coronary balloon dilatation catheter 24 (FIG. 3) using a guide wire 26. The wall at a distal tip 20b of catheter tube 20 has embedded therein a micro-manometer 28, that is, a pressure transducer for measuring the blood-pressure and for outputting the electrical signal P corresponding to the detected arterial pressure. Electrical leads 30 leading from connectors 32 at the proximal end 20a of catheter tube 20 to micromanometer 28 are also embedded within the wall of the catheter tube 20.

Referring to FIG. 3, micro-manometer 28 is embedded in the wall of catheter tube 20 so that the outer face of the micro-manometer is directly exposed to the blood in the artery, and so that the inner face of the embedded micro-manometer is covered by the inner face of the wall of the catheter tube 20. Thus, micro-manometer 28 directly senses the blood pressure on the outer face of the micro-manometer, and generates the electrical signal P representing a precise measurement of the arterial blood pressure, which electrical signal is transmitted through leads 30 and connectors 32 to the differentiating circuit 4 of FIG. 1.

The balloon dilatation catheter 24, illustrated in FIG. 3, is used particularly when there is an obstruction in the coronary artery. When so used, the flexible catheter tube 20 is first inserted into the artery to bring its distal end 20b to the ostium of the coronary artery. The balloon dilatation catheter 24 is inserted through the catheter tube to the point of the obstruction, whereupon the balloon is inflated to dilate the coronary artery at the place of the obstruction. During this procedure, the arterial pressure is continuously detected by micro-manometer 28 and is used for continuously monitoring the systemic vascular resistance in accordance with the above-described method as illustrated in FIG. 1. A precise measurement of the arterial pressure for this purpose is produced because the micro-manometer 28 is embedded in the outer face of the catheter tube 20 so as to be exposed to the blood in the artery. This permits a more precise detection of the blood pressure, since the micro-manometer is not significantly influenced by the inflation of the balloon in catheter 24.

An increase by at least 60% in the systemic vascular resistance of the subject, as detected by detector 14 in FIG. 1, would be strongly indicative of a myocardial ischemic episode or condition, and would be indicated by indicator 16 so as to alert the attendant to take the appropriate action.

Myocardial monitoring and detection is described above with respect to an invasive procedure, involving heart catheterization or balloon angioplasty dilatation of the coronary arteries. While this is a preferred procedure, ischemia monitoring and detection can also be performed in accordance with the present invention using a non-invasive procedure, such as by the use of pressure cuffs. Also, while the described technique monitors the systemic vascular resistance in accordance with the method and apparatus described in our U.S. Pat. No. 4,429,701, it will be appreciated that other methods for monitoring systemic vascular resistance can also be used.

Other variations, modifications and applications of the invention will be apparent to those practiced in the field and are within the scope of the following claims.

What is claimed is:

1. A method for detecting myocardial ischemia in a subject comprising the steps of:
   monitoring the systemic vascular resistance of the subject; and
   detecting the presence of myocardial ischemia in a subject when the monitored systemic vascular resistance of the subject increases by at least 60%, thereby indicating the presence of myocardial ischemia.

2. The method according to claim 1, wherein the monitoring step comprises the steps of:
   A. detecting the arterial pressure of the subject and generating in response thereto a blood pressure signal having a waveform in accordance with the detected arterial pressure;
   B. differentiating said blood pressure signal to produce a dP/dt signal having a waveform varying in accordance with the rate at which the blood pressure signal varies;
   C. detecting the peak of said dP/dt signal to determine the peak dP/dt;
   D. determining a value which is substantially equal to the arterial pressure at the time of said peak dP/dt;
   E. dividing said latter value by said peak dP/dt signal, which thereby produces a measurement corresponding to the systemic vascular resistance of said cardiovascular system.

3. The method according to claim 2, wherein the pressure of the femoral artery is detected.

4. The method according to claim 1, wherein said monitoring step includes the step of detecting the pressure of the femoral artery.

5. Apparatus for detecting myocardial ischemia in a subject comprising:
   monitoring means for monitoring the systemic vascular resistance of the subject, and
   indicator means for detecting the presence of myocardial ischemia in the subject increases by at least 60%, thereby indicating the presence of myocardial ischemia in the subject.

6. The apparatus according to claim 5 wherein said monitoring means comprises:
   A. means for detecting the arterial pressure of the subject and for generating in response thereto a blood pressure signal having a waveform varying in accordance with the detected arterial pressure;
   B. means for differentiating said blood pressure signal to produce a dP/dt signal having a waveform varying in accordance with the rate at which the blood pressure signal varies;
   C. means for detecting the peak of said dP/dt signal to determine the peak dP/dt;
   D. means for determining a value which is substantially equal to the arterial pressure at the time of said peak dP/dt; and
   E. means for dividing said latter value by said peak dP/dt, thereby producing a measurement corresponding to the systemic vascular resistance of said cardiovascular system.

* * * * *

UNITED STATES PATENT AND TRADEMARK OFFICE
CERTIFICATE OF CORRECTION

PATENT NO.   :   4,821,735
DATED        :   April 18, 1989
INVENTOR(S)  :   Daniel Goor et al It is certified that error appears in the above—identified patent and that said Letters Patent is hereby corrected as shown below:

Column 1, line 45, before "subject's" insert
--Ischemia can be associated with elevation
or depression of the--

Column 6, line 38 (Claim 5), before "increases"
insert --when the monitored systemic vascular
resistance of the subject--

Signed and Sealed this

Twenty-eighth Day of November 1989

Attest:

JEFFREY M. SAMUELS

Attesting Officer        Acting Commissioner of Patents and Trademarks